United States Patent
Dasberg et al.

(10) Patent No.: US 8,741,959 B2
(45) Date of Patent: Jun. 3, 2014

(54) PARACETAMOL FOR PARENTERAL ADMINISTRATION

(75) Inventors: David Dasberg, Bad Homburg (DE); Georg Achleitner, Graz (AT); Christiane Aichholzer, Graz (AT)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/262,650

(22) PCT Filed: Apr. 19, 2010

(86) PCT No.: PCT/EP2010/002368
§ 371 (c)(1),
(2), (4) Date: Oct. 25, 2011

(87) PCT Pub. No.: WO2010/121762
PCT Pub. Date: Oct. 28, 2010

(65) Prior Publication Data
US 2012/0035267 A1 Feb. 9, 2012

(30) Foreign Application Priority Data
Apr. 22, 2009 (EP) .................................... 09005630

(51) Int. Cl.
- *A01N 37/18* (2006.01)
- *A61K 31/16* (2006.01)
- *C07C 209/00* (2006.01)
- *A61K 9/00* (2006.01)

(52) U.S. Cl.
USPC ............. 514/630; 514/629; 564/4; 564/5; 564/6; 564/7; 424/400

(58) Field of Classification Search
USPC ........... 514/630, 629; 564/4, 5, 6, 7; 424/400
See application file for complete search history.

(56) References Cited

U.S. PATENT DOCUMENTS

| | | | |
|---|---|---|---|
| 6,028,222 | A | 2/2000 | Dietlin et al. |
| 6,992,218 | B2 * | 1/2006 | Dietlin et al. ................... 564/4 |
| 2005/0203175 | A1 | 9/2005 | Tseti |
| 2006/0084703 | A1 | 4/2006 | Nguyen-Xuan |
| 2006/0292214 | A1 | 12/2006 | Jenkins et al. |
| 2009/0143474 | A1 * | 6/2009 | Royal et al. ................... 514/629 |

FOREIGN PATENT DOCUMENTS

| | | |
|---|---|---|
| DE | 279405 | 6/1990 |
| EP | 0916347 | 5/1999 |
| EP | 0858329 | 6/2003 |
| EP | 1752139 | 2/2007 |
| EP | 1889607 | 2/2008 |
| FR | 2809619 | 12/2001 |
| KR | 930011994 | 12/1993 |
| WO | 00/07588 | 2/2000 |
| WO | 01/08662 | 2/2001 |
| WO | 02/072080 | 9/2002 |
| WO | 03/033026 | 4/2003 |
| WO | 2008/007150 | 1/2008 |

OTHER PUBLICATIONS

Guardiola—English translation, EP 1752139, 2007.*
Integrated Clinical Report (Insulin Detemir, Jul. 17, 2006, p. 1-3).*
Database WPI Week 199444 Thomson Scientific, London, GB; AN 1994-355463 (XP002030817) & KR 930 011 994 (Dec. 23, 1993) abstract.
Schug, Stephan A., "Update on Acute Pain Service 2006" [retrieved from internet: http://www.rph.wa.gov.au/anaesth/downloads/APS%20Update%202006.pdf (date: Jan. 14, 2013); 46 pages (in particular slide 4).
Perfalgan®, Consumer Medicine Information, May 2008 (1 page).

* cited by examiner

*Primary Examiner* — Sreeni Padmanabhan
*Assistant Examiner* — Uma Ramachandran
(74) *Attorney, Agent, or Firm* — Occhiuti & Rohlicek LLP

(57) ABSTRACT

The invention relates to an aqueous pharmaceutical composition, preferably an infusion solution, for parenteral administration which contains paracetamol and has an electrical conductivity of not more than 200 $\mu S\ cm^{-1}$.

24 Claims, No Drawings

PARACETAMOL FOR PARENTERAL ADMINISTRATION

CROSS REFERENCE TO RELATED APPLICATIONS

This application is the national stage of international application no. PCT/EP2010/002368, filed on Apr. 19, 2010, which claims the priority of European application no. 09005630.0, filed on Apr. 22, 2009. The contents of both applications are incorporated herein.

The invention relates to pharmaceutical formulations of the active ingredient paracetamol (acetaminophen), which are suitable for parenteral administration, in particular infusion.

Paracetamol is a very widely employed active ingredient having excellent tolerability (cf., for example, G. G. Graham et al., Drug Safety, 2005, 28(3), 227-40). Paracetamol is commercially obtainable in numerous pharmaceutical forms, in particular as an oral administration form. In certain cases, for example in the course of intensive care or if oral administration is not possible for certain reasons, parenteral administration of paracetamol is desirable.

The pharmacopeia understands parenterals as meaning sterile preparations that are intended for injection, infusion or implantation. Parenterals must in principle be prepared with particular care in order to guarantee non-irritancy and to avoid microbial and particulate contamination. Excipients are especially substances for improving solubility, substances for isotonicization, buffers, antioxidants, chelating agents, preservatives, emulsifiers and excipients for prolonging action.

Aqueous parenterals must be iso-osmotic or approximately iso-osmotic to the plasma or lymph. In the case of severe hypo- or hyperosmotic differences, erythrocyte damage or tissue irritation usually occurs. In the case of intravenous administration of strong hypo-osmotic solutions hemolysis occurs, in the case of supply of relatively large amounts of hyperosmotic solutions plasmolysis occurs.

The pH of aqueous parenterals also plays an important role. Blood serum is provided with the four buffer systems carbonic acid/hydrogencarbonate, plasma proteins, primary/secondary phosphate and hemoglobin/oxyhemoglobin. The pH of the blood is between 7.30 and 7.45. An approximation of the pH of infusion solutions to the physiological pH range (isohydria) is often not possible for stability reasons. Only a best-possible approximation to the physiological pH range (euhydria) is then carried out. The tolerance range for infusion solutions is in general between pH 3.0 and 10.5. Depending on the difference of the actual pH from the physiological pH range, a sufficiently slow infusion is then necessary to make possible an approximation of the physiological pH range to the buffer systems of the blood.

Buffering of infusion solutions, e.g. with acetate, phosphate or citrate buffers, has the disadvantage that the natural pH stabilization of the blood is superposed. In order to retain the natural pH stabilization of the blood, buffering of infusion medicaments should therefore not take place if possible. The adjustment of the pH with strong acids or bases (e.g. HCl or NaOH), on the other hand, does not result in any buffer action and is therefore less questionable.

Infusion solutions of paracetamol are known in the prior art.

In the Federal Republic of Germany, an infusion solution of paracetamol is marketed under the name Perfalgan®. The infusion solution is indicated for short-term treatment of moderately severe pain, particularly after operations, and for the short-term treatment of fever if intravenous administration is clinically justified because of urgently necessary pain or fever treatment or if other types of administration are not possible. The administration takes place as a 15-minute infusion. In addition to paracetamol, the infusion solution contains as other constituents cysteine hydrochloride monohydrate, sodium monohydrogenphosphate dihydrate, hydrochloric acid, mannitol, sodium hydroxide and water for injection. The content of sodium is stated as 0.04 mg/ml. The shelflife is stated as 2 years, where storage should not take place above 30° C. or in a refrigerator.

EP-A 916 347 discloses buffered paracetamol injection forms based on organic solvents, in particular ethanol and benzyl alcohol. Chelating agents and antioxidants are added as stabilizers.

US-A 2005/0203175 discloses buffered compositions for parenteral administration of paracetamol in combination with lidocaine HCl, which contain, inter alia, organic solvents, chelating agents and antioxidants.

WO 02/072080 relates to buffered aqueous solutions of paracetamol and antioxidants selected from the group consisting of ascorbic acid, N-acetyl-1-cysteine and other SH group-containing stabilizers. The solutions are rendered isotonic using NaCl.

U.S. Pat. No. 6,028,222 discloses buffered aqueous solutions of paracetamol which contain a free radical scavenger or free radical antagonists.

WO 03/033026 relates to aqueous solutions of pracetamol which contain propylene glycol and citrate buffer and are obtainable by means of a designated heat treatment.

EP-A 1 889 607 discloses buffered aqueous solutions of paracetamol, which contain glucose, fructose or gluconate and formaldehyde sulfoxylate, sodium sulfite or sodium dithionite.

EP-A 1 752 139 relates to aqueous solutions of paracetamol and antioxidants selected from the group consisting of ascorbic acid, N-acetyl-1-cysteine and other SH group-containing stabilizers. The solutions are rendered isotonic using NaCl and have an oxygen content of less than 1 mg/l.

U.S. Pat. No. 6,992,218 and FR-A 2 809 619 relate to processes for the preparation of buffered, aqueous solutions of paracetamol having an oxygen content of less than 2 ppm.

US 2006/0084703 discloses aqueous formulations of paracetamol, which contain buffer, isotonicizing agent and a paracetamol dimer.

US 2006/0292214 relates to compositions which contain paracetamol in nanoparticulate form.

KR 930 011 994 discloses, according to the abstract, compositions, inter alia, for the parenteral administration of paracetamol, in which the active ingredient is dissolved in polyethylene glycol and propylene glycol. The compositions are suitable for the production of tablets, capsules, syrups, suppositories and injection preparations. Information on aqueous compositions cannot be taken, however, from the abstract, in particular also not infusion solutions.

WO 00/07588 relates to an essentially anhydrous paracetamol composition, which contains polyethylene glycol and alcohol and is diluted with water before use to give an injectable solution.

US 2005/203175 discloses a paracetamol composition which contains chelating agent, antioxidant and buffer.

WO 01/08662 relates to an essentially anhydrous paracetamol composition for nasal administration.

WO 2008/007150 discloses a paracetamol nanodispersion for oral administration.

The pharmaceutical compositions known from the prior art for the parenteral administration of paracetamol, however, are not satisfactory in every respect. Paracetamol is comparatively poorly soluble and sensitive to oxidation, which is why appropriate measures are customarily taken in order to guarantee an adequate storage stability of the compositions.

Thus the pharmaceutical compositions for parenteral administration of paracetamol are customarily buffered, such that the natural buffer action of the blood is superposed by the buffers and, where appropriate, an only comparatively slow infusion is possible. In the case of phosphate buffers, in particular with divalent metal cations ($Ca^{2+}$, $Mg^{2+}$), insoluble complexes can be formed. This can have an adverse effect, not only in patients with appropriate deficiency symptoms, but also complicates co-infusion with appropriate electrolyte solutions, which can be indicated under certain circumstances.

Furthermore, many of the known pharmaceutical compositions contain comparatively high electrolyte concentrations, in particular also sodium ions, which can lead to an osmotic shift of water from the cells into the interstitium.

Moreover, the pharmaceutical compositions for the parenteral administration of paracetamol customarily contain a multiplicity of different ingredients, which is disadvantageous, inter alia, from the economic point of view. Because of the particular requirements of parenterals, particular purity criteria must be maintained and regularly monitored analytically. Thus the known pharmaceutical compositions for the parenteral administration of paracetamol customarily contain certain antioxidants, which can cause incompatibilities and side effects. If such anti-oxidants are dispensed with, this customarily results in a lower storage stability.

Other pharmaceutical compositions for the parenteral administration of paracetamol are prepared in anhydrous form, in particular in the form of alcoholic solutions, which must be diluted immediately before administration, for example with water. These compositions are thus still not ready for use as such, but require special, relatively involved preparation measures before they can be used. The alcoholic aqueous compositions resulting therefrom have considerable disadvantages, not least because of the alcohol content, and are unsuitable, for example, for infusion. The preparation measures, such as dilution, also always entail the danger of introducing contamination, which is risky with sterility criteria.

The invention is based on the object of making available pharmaceutical compositions for parenteral administration, which have advantages compared to the compositions of the prior art.

This object is achieved by the subject matter of the patent claims.

It has surprisingly been found that paracetamol can be stabilized against oxidative degradation if the electrolyte concentration is kept low. The addition of electrolytes leads to destabilization.

If the electrical conductivity is taken as a measure of the content of electrolytes, the storage stability decreases with increasing electrical conductivity. It is possible by this means to prepare compositions for parenteral administration of paracetamol, in particular infusion solutions, which manage with a minimum of ingredients and nevertheless have an adequate storage stability.

If consistently nonionic or zwitterionic compounds, which outwardly are electrically neutral, are added as ingredients, these virtually do not increase the electrical conductivity of the composition, by means of which the high storage stability of the composition is retained and, if required, depending on the type of ingredient, can be further improved.

The invention relates to an aqueous pharmaceutical composition for parenteral administration, preferably in the form of an infusion solution, which contains paracetamol and has an electrical conductivity of at most 200 $\mu S\ cm^{-1}$.

The composition according to the invention, preferably an infusion solution, is aqueous. Since it is intended for parenteral administration, it preferably contains water for injection (Ph. Eur.). Preferably, water for injection is the only liquid constituent of the composition according to the invention. Thus the composition according to the invention preferably contains no organic solvents. Among these come all essentially low molecular weight organic compounds known to the person skilled in the art, which are employed exclusively for the purpose of increasing the solubility of paracetamol in water. These especially include alcohols, in particular $C_1$-$C_6$-alkanols such as ethanol, propylene glycol, glycerol, benzyl alcohol and other low molecular weight organic compounds that contain hydroxyl groups. Further representatives are higher molecular weight substances, in particular polyethylene glycol, polypropylene glycol and their mixtures or copolymers. Particularly preferably, the composition according to the invention contains no organic solvent selected from the group consisting of $C_1$-$C_6$-alkanols, propylene glycol and polyethylene glycol (PEG).

Infusion solutions and injection solutions are to be differentiated from one another in principle.

Injection is the injecting of sterile medicaments into the body using a syringe and a hollow needle. The volume of an injection is customarily 0.1 to 20 ml. In contrast to infusion, the medicament is administered in the course of seconds up to a few minutes, in which manual pressure is exerted on the syringe. Injections often do not take place intravenously but, for example, subcutaneously or intramuscularly. In this case, either a local action should be achieved or else, for a systemic action, a type of active ingredient depot is formed locally, from where the active ingredient is released gradually into the circulation. If medicaments are injected intravenously, great caution is demanded. It is very important that the rate during the administration (between 1-3 ml per minute) is maintained exactly. At most 5 ml may be injected in this way. If the dose necessary is higher, the medicament must be injected in a carrier solution and given by means of a brief infusion. The basic difference for infusion is also clear due to the fact that in the case of injections care is customarily to be taken that larger vessels in particular are not hit with the needle, since otherwise an unintentional intravenous or intra-arterial administration would be achieved, which can cause, for example, an anaphylactic shock.

Infusion is customarily a slow, usually dropwise inflow of relatively large (pharmaceutical-containing) amounts of liquid into the body, in which, depending on the duration of the infusion, a differentiation can be made between continuous infusions (several hours, often also uninterrupted for 24 hours) and short-term infusions (less than 3 hours, often 15-30 minutes). The inflow customarily takes place because of the hydrostatic pressure of the liquid column in the supply, in contrast to injection, but not by active exertion of pressure. Infusions often take place intravenously. The composition of infusion solutions therefore usually differs fundamentally from the composition of injection solutions, in particular also with respect to the active ingredient concentration.

Preferentially, in the composition according to the invention, preferably an infusion solution, all ingredients are present in completely dissolved form, i.e. it is preferably not a dispersion, neither an emulsion nor a suspension. The composition according to the invention is preferably particle- and discoloration-free. In particular, the composition according to the invention preferably also contains no nanoparticles.

The composition according to the invention, preferably an infusion solution, contains paracetamol (acetaminophen). The paracetamol is preferably present in completely dissolved form. The concentration of the paracetamol in the composition according to the invention is preferably below its saturation concentration, particularly preferably at least 95% below its saturation concentration at room temperature.

In a preferred embodiment, the concentration of the paracetamol is in the range from $10.0\pm7.5$ g $l^{-1}$, $10.0\pm6.0$ g $l^{-1}$, $10.0\pm5.0$ g $l^{-1}$, $10.0\pm4.0$ g $l^{-1}$, $10.0\pm3.0$ g $l^{-1}$ or $10.0\pm2.5$ g $l^{-1}$; more preferably $10.0\pm2.0$ g $l^{-1}$, even more preferably $10.0\pm1.5$ g $l^{-1}$, most preferably $10.0\pm1.0$ g $l^{-1}$, and in particular $10.0\pm0.5$ g $l^{-1}$, based on the composition.

In a preferred embodiment, the content of paracetamol is either less than 1.2% by weight or more than 1.3% by weight, based on the composition.

The composition according to the invention, preferably an infusion solution, can contain further active ingredients in addition to paracetamol. Preferably, the composition according to the invention, however, contains paracetamol as the only active ingredient.

The composition according to the invention, preferably an infusion solution, has an electrical conductivity of at most 200 μS $cm^{-1}$. The measurement of the electrical conductivity of aqueous solutions is known to the person skilled in the art and suitable measuring apparatuses are obtainable commercially. The electrical conductivity is preferably measured at room temperature. Preferably, the electrical conductivity of the composition according to the invention is at most 190 μS $cm^{-1}$, at most 180 μS $cm^{-1}$, at most 170 μS $cm^{-1}$, at most 160 μS $cm^{-1}$, at most 150 μS $cm^{-1}$, at most 140 μS $cm^{-1}$, at most 130 μS $cm^{-1}$, at most 120 μS $cm^{-1}$ or at most 110 μS $cm^{-1}$; more preferably at most 100 μS $cm^1$, at most 90 μS $cm^{-1}$, at most 80 μS $cm^{-1}$, at most 70 μS $cm^{-1}$, or at most 60 μS $cm^{-1}$; even more preferably at most 50 μS $cm^{-1}$, at most 40 μS $cm^{-1}$, or at most 30 μS $cm^{-1}$; most preferably at most 25 μS $cm^{-1}$, at most 20 μS $cm^{-1}$ or at most 15 μS $cm^{-1}$; and in particular at most 12.5 μS $cm^{-1}$, at most 10 μS $cm^1$ or at most 7.5 μS $cm^{-1}$.

The composition according to the invention, preferably an infusion solution, is therefore distinguished by a comparatively low electrical conductivity. Thus in comparison the electrical conductivity of an isotonic saline solution (0.9% by weight of NaCl) is more than 7500 μS $cm^{-1}$. The electrical conductivity of aqueous compositions is essentially influenced by ions. It can be predicted on the basis of the square root law according to Kohlrausch or the Debye-Hückel-Onsager theory. As illustrated in more detail in the experimental section, paracetamol itself virtually does not contribute to the electrical conductivity (10 g of paracetamol in 1000 ml of water: about 4 μS/cm). An addition of 100 mg of NaCl to this active ingredient solution (0.01% by weight of NaCl), however, already leads to an increase in the electrical conductivity to about 200 μS/cm.

In connection with pharmaceutical compositions for parenteral administration, preferably infusion solutions, electrolytes and buffers in particular have an influence on the electrical conductivity. Accordingly, the composition according to the invention contains, if at all, at most a comparatively small amount of electrolytes and/or buffer substances.

In a preferred embodiment, the composition according to the invention, preferably an infusion solution, contains virtually no trivalent electrolytes, e.g. $PO_4^{3-}$ and $HOC(CO_2^-)_3$. In another preferred embodiment, the composition according to the invention contains virtually no divalent electrolytes, e.g. $Ca^{2+}$, $Mg^{2+}$, $HPO_4^{2-}$ and $HOC(CO_2^-)_2CO_2H$. In a further preferred embodiment, the composition according to the invention contains virtually no monovalent electrolytes, e.g. $Na^+$, $K^+$, $NH_4^+$, $Cl^-$, $CH_3CO_2^-$, $H_2PO_4^-$ and $HOCCO_2^-(CO_2H)_2$.

In a preferred embodiment, the composition according to the invention, preferably an infusion solution, has a buffer capacity β of at most 5 mmol $l^{-1}$ $pH^{-1}$. The definition and the determination of the buffer capacity β are known to the person skilled in the art. In general, the buffer capacity is that amount of substance of a strong proteolyte (acid or base), which is necessary in order to change the pH of the composition by one unit. Preferably, the measurement of the buffer capacity takes place at room temperature.

Preferably, the composition according to the invention, preferably an infusion solution, has a buffer capacity β of at most 4.5 mmol $l^{-1}$ $pH^{-1}$, at most 4.0 mmol $l^{-1}$ $pH^{-1}$, at most 3.5 mmol $l^{-1}$ $pH^{-1}$, at most 3.0 mmol $l^{-1}$ $pH^{-1}$, at most 2.5 mmol $l^{-1}$ $pH^{-1}$, at most 2.0 mmol $l^{-1}$ $pH^{-1}$, at most 1.5 mmol $l^{-1}$ $pH^{-1}$, or at most 1.0 mmol $l^1$ $pH^{-1}$; preferably at most 0.9 mmol $l^{-1}$ $pH^{-1}$, at most 0.8 mmol $l^{-1}$ $pH^{-1}$, at most 0.7 mmol $l^{-1}$ $pH^{-1}$, at most 0.6 mmol $l^{-1}$ $pH^{-1}$, at most 0.5 mmol $l^{-1}$ $pH^{-1}$, at most 0.4 mmol $l^{-1}$ $pH^{-1}$, at most 0.3 mmol $l^{-1}$ $pH^{-1}$, at most 0.2 mmol $l^{-1}$ $pH^{-1}$, or at most 0.1 mmol $l^{-1}$ $pH^{-1}$; even more preferably at most 0.09 mmol $l^{-1}$ $pH^{-1}$, at most 0.08 mmol $l^{-1}$ $pH^{-1}$, at most 0.07 mmol $l^{-1}$ $pH^{-1}$, at most 0.06 mmol $l^{-1}$ $pH^{-1}$, at most 0.05 mmol $l^{-1}$ $pH^{-1}$, at most 0.04 mmol $l^{-1}$ $pH^{-1}$, at most 0.03 mmol $l^{-1}$ $pH^{-1}$, at most 0.02 mmol $l^{-1}$ $pH^{-1}$ or at most 0.01 mmol $l^{-1}$ $pH^{-1}$; most preferably at most 0.009 mmol $l^{-1}$ $pH^{-1}$, at most 0.008 mmol $l^{-1}$ $pH^{-1}$, at most 0.007 mmol $l^{-1}$ $pH^{-1}$, at most 0.006 mmol $l^{-1}$ $pH^{-1}$, or at most 0.005 mmol $l^{-1}$ $pH^{-1}$; particularly preferably the composition according to the invention is virtually unbuffered.

Preferably, the composition according to the invention, preferably an infusion solution, has a pH in the range from 5.0 to 7.5. In a preferred embodiment, the composition according to the invention has a pH in the range from $5.5\pm0.5$, more preferably $5.5\pm0.4$, even more preferably $5.5\pm0.3$, most preferably $5.5\pm0.2$ and in particular $5.5\pm0.1$. In another preferred embodiment, the composition according to the invention has a pH in the range from $6.0\pm0.5$, more preferably $6.0\pm0.4$, even more preferably $6.0\pm0.3$, most preferably $6.0\pm0.2$ and in particular $6.0\pm0.1$. In a further preferred embodiment, the composition according to the invention has a pH in the range from $6.5\pm0.5$, more preferably $6.5\pm0.4$, even more preferably $6.5\pm0.3$, most preferably $6.5\pm0.2$ and in particular $6.5\pm0.1$. In another preferred embodiment, the composition according to the invention has a pH in the range from $7.0\pm0.5$, more preferably $7.0\pm0.4$, even more preferably $7.0\pm0.3$, most preferably $7.0\pm0.2$ and in particular $7.0\pm0.1$.

In a particularly preferred embodiment, the pH of the composition according to the invention, preferably an infusion solution, is native, i.e. it is fixed by the ingredients and influenced neither by the addition of buffer nor by the addition of strong acid or base.

Preferably, the composition according to the invention, preferably an infusion solution, contains one or more nonionic isotonicizing agents. Suitable nonionic isotonicizing agents are known to the person skilled in the art, in particular glucose, fructose and mannitol. Preferably, the nonionic isotonicizing agent is a sugar alcohol, in particular mannitol (mannite).

The concentration of the nonionic isotonicizing agent, preferably mannitol, is preferably in the range from $35\pm25$ g$l^{-1}$, more preferably $35\pm20$ g$l^{-1}$, even more preferably $35\pm15$ g$l^{-1}$, most preferably $35\pm10$ g$l^{-1}$, and in particular $35\pm5$ g$l^{-1}$, based on the composition. In a preferred embodiment, the absolute content of mannitol is either less than 0.91% by weight or more than 1.17% by weight, based on the composition, preferably an infusion solution.

Preferably, the proportion by weight of the nonionic isotonicizing agent, preferably mannitol, is greater than the proportion by weight of paracetamol in the composition according to the invention, preferably an infusion solution. Preferably, the relative weight ratio of nonionic isotonicizing agent:paracetamol is >1:1, more preferably >1.5:1, even more preferably >2:1, most preferably >2.5:1 and in particular >3:1 or >3.5:1. In a preferred embodiment, the relative weight ratio of paracetamol to mannitol is either greater than 1:0.7 or less than 1:1.

In a preferred embodiment, the composition according to the invention, preferably an infusion solution, contains cysteine, if appropriate additionally to mannitol. Although cysteine is present at pH 7 as a zwitterion, it is interpreted according to the invention because of its electroneutrality as a nonionic isotonicizing agent, which virtually does not contribute to the electrical conductivity of the composition. It was found that cysteine at pH 5.5 to 7 has no buffer properties at all.

The concentration of the cysteine is preferably in the range from $0.1\pm0.09$ g$l^{-1}$, more preferably $0.1\pm0.08$ g$l^{-1}$, even more preferably $0.1\pm0.07$ g$l^{-1}$, most preferably $0.1\pm0.06$ g$l^{-1}$, and in particular $0.1\pm0.05$ g$l^{-1}$, based on the composition, preferably an infusion solution.

Preferably, the proportion by weight of paracetamol is greater than the proportion by weight of cysteine in the composition according to the invention, preferably an infusion solution. Preferably, the relative weight ratio of paracetamol:cysteine is >50:1, more preferably >60:1, even more preferably >70:1, most preferably >80:1 and in particular >90:1 or >95:1.

In a preferred embodiment, the composition according to the invention, preferably an infusion solution, contains both mannitol and cysteine. In this case, the proportion by weight of mannitol is preferably greater than the proportion by weight of cysteine in the composition according to the invention. Preferably, the relative weight ratio of mannitol:cysteine is >100:1, more preferably >200:1, even more preferably >250:1, most preferably >300:1 and in particular >350:1 or >360:1.

In a preferred embodiment, the composition according to the invention, preferably an infusion solution, contains, if at all, altogether at most 100 mmol/l of alkali metal cations, more preferably altogether at most 10 mmol/l, even more preferably altogether at most 1.0 mmol/l, most preferably altogether at most 0.1 mmol and in particular altogether at most 0.01 mmol/l. In a preferred embodiment, the composition according to the invention contains virtually no salt, neither dissolved nor solid. In this composition, zwitterionic compounds under isoelectric conditions, e.g. amino acids such as cysteine, are not interpreted as salts.

In a preferred embodiment, the composition according to the invention, preferably an infusion solution, contains no chelating agents, e.g. EDTA.

In a preferred embodiment, the composition according to the invention, preferably an infusion solution, contains altogether at most 5 ingredients, i.e. in addition to paracetamol and water the composition consists of at most 3 further ingredients. Ionic compounds which dissociate in water to give cations and anions count here as 2 compounds. Particularly preferably, the composition according to the invention contains at most 4 ingredients. Particularly preferably, the composition according to the invention consists of water, paracetamol and mannitol and/or cysteine.

In a particularly preferred embodiment, the composition according to the invention, preferably an infusion solution, contains, in addition to water, paracetamol and one or more non-ionic isotonicizing agents, no further ingredients at all.

The composition according to the invention is preferably ready for use, i.e. it can preferably be administered immediately, in particular without specific preparation measures (ready-to-use). Thus it is preferably not necessary for the composition according to the invention to be diluted or for further ingredients to have to be added before the composition can be administered to the patient.

The composition according to the invention is intended for parenteral administration, in particular for intravenous infusion, i.e. it is preferably an infusion solution. For this purpose, it is necessary for the composition to have a physiologically tolerable osmolarity (or osmolality). Preferably, the composition according to the invention has an osmolarity of at least 0.22 osmol $l^{-1}$, more preferably at least 0.23 osmol $l^{-1}$, more preferably at least 0.24 osmol $l^{-1}$, even more preferably at least 0.25 osmol $l^{-1}$, most preferably at least 0.26 osmol $l^{-1}$, and in particular at least 0.27 osmol $l^{-1}$. Preferably, the composition according to the invention has an osmolarity of at most 0.36 osmol $l^{-1}$, more preferably at most 0.34 osmol $l^{-1}$, more preferably at most 0.32 osmol $l^{-1}$, even more preferably at most 0.30 osmol $l^{-1}$, most preferably at most 0.29 osmol $l^{-1}$, and in particular at most 0.28 osmol $l^{-1}$. In comparison, an isotonic saline solution contains 0.9% (mass percent) of sodium chloride and corresponds with an osmolarity of 308 mosmol/l approximate to that of blood plasma. The theoretical osmolarity of a Ringer infusion solution is 309 mOsm/l. The theoretical osmolarity of a Ringer lactate solution is between 262 and 293 mOsm/l.

The composition according to the invention, preferably an infusion solution, is distinguished by an outstanding storage stability. It has surprisingly been found that with low electrical conductivity, and accompanying it, correspondingly lower electrolyte concentration, buffer substances can be completely dispensed with and an adequate storage stability is nevertheless achieved. Preferably, the content of paracetamol after storage at 60° C. for 4 weeks in closed vessels is at least 99.0% of the paracetamol originally contained in the composition, i.e. before storage, more preferably at least 99.2%, even more preferably at least 99.4%, most preferably at least 99.6% and in particular at least 99.8%, preferably under the conditions illustrated more closely in the experimental section.

The composition according to the invention, preferably an infusion solution, can be prepared by conventional processes known to the person skilled in the art.

Preferably, firstly here
A) water for injection with an oxygen content of less than 0.50 mg/l is introduced;
B) paracetamol and the further ingredients are dissolved in the water A) in the desired amounts with as extensive exclusion of oxygen as possible; and
C) if required the pH of the solution is adjusted to the desired value by addition of a physiologically tolerable acid or base.

Expediently
D) the solution adjusted to the desired pH is then filtered through a 0.2 μm membrane filter, subsequently filled into containers for infusion solutions and heat-sterilized at 121° C. for 15 min.

A further preferred variant of the process for the preparation of the solution according to the invention provides for an inert gas to be led through the water in step A) for driving out the oxygen and that during mixing in step B) and if appropriate in all further steps for work to be carried out under an inert gas atmosphere.

A further aspect of the invention relates to containers which contain the composition according to the invention. Here, the composition according to the invention is preferably present as a "Ready-to-use" preparation, i.e. can be used immediately. In particular, preferably no dilution or dissolution steps are necessary before use.

The composition according to the invention is preferably packaged in containers customary for parenteral preparations. The containers can be bottles or bags, such as are customary for injection-ready solutions. Containers made of glass or plastic are preferred. If they are plastic containers, these preferably consist of a material based on polyolefins and are optionally surrounded by a second bag, which contains an oxygen barrier layer, possibly with an oxygen absorber between the bags. Suitable packaging materials are known to the person skilled in the art. In this connection, reference can be made fully, for example, to E. Bauer, Pharmaceutical Packaging Handbook, Informa Health Care 2009; or D. A. Dean, Pharmaceutical Packaging Technology, Taylor & Francis 2000.

The composition according to the invention can be packaged under protective gas, for example under $N_2$, $CO_2$ or Ar. In a preferred embodiment, the composition according to the invention has a content of dissolved oxygen of at most 50 ppm, more preferably at most 20 ppm, even more preferably at most 10 ppm, most preferably at most 5 ppm and in particular at most 2 ppm or at most 1 ppm.

In a preferred embodiment, the composition according to the invention is an infusion solution which is prepared for intravenous infusion over a period of time of 2 minutes to 24 hours, more preferably over a period of time of 3 minutes to 6 hours, even more preferably 5 minutes to 1 hour, most preferably 10 minutes to 45 minutes and in particular 15 minutes.

A further aspect of the invention relates to the composition described above, preferably an infusion solution, for the treatment of pain or the use of paracetamol for the production of a composition described above for the treatment of pain. Preferably the pain is moderately strong pain, preferably postoperative pain.

In a preferred embodiment, the patient is a geriatric or paediatric patient.

The following examples serve to illustrate the invention, but are not designed to be restrictive:

Aqueous solutions of paracetamol and further ingredients were prepared. The electrical conductivity of the solutions was measured and the storage stability of paracetamol was determined by means of the formation of degradation products (for the formation of the dimer cf., for example, D. W. Pottert et al, J Biol Chem, 1985, 280(22), 12174-80; W. Clegg et al., Acta Crystallographica, 1998, C54, 1881-2).

The results are summarized in the following two tables:

| | in 500 ml of H$_2$O for injection | | | electrical | dimer [% rel. to paracetamol] | | | | impurities overall [% rel. to paracetamol] | | | |
|---|---|---|---|---|---|---|---|---|---|---|---|---|
| Ex. | paracetamol [g] | mannitol [g] | NaCl [mg] | conductivity [µS cm$^{-1}$] | autoclaved | 1 week 60° C. | 2 weeks 60° C. | 4 weeks 60° C. | autoclaved | 1 week 60° C. | 2 weeks 60° C. | 4 weeks 60° C. |
| 1 | 5.0 | — | — | 3.15 | 0.018 | 0.053 | 0.083 | 0.104 | 0.050 | 0.097 | 0.141 | 0.177 |
| 2 | 5.0 | 18.35 | — | 3.24 | 0.012 | 0.030 | 0.045 | 0.060 | 0.041 | 0.072 | 0.095 | 0.128 |
| 3 | 5.0 | — | 1.0 | 5.22 | 0.037 | 0.094 | 0.093 | 0.112 | 0.079 | 0.161 | 0.161 | 0.191 |
| 4 | 5.0 | — | 2.5 | 11.45 | 0.028 | 0.062 | 0.101 | 0.142 | 0.067 | 0.111 | 0.170 | 0.228 |
| 5 | 5.0 | — | 12.2 | 49.6 | 0.021 | 0.077 | 0.101 | 0.128 | 0.056 | 0.130 | 0.172 | 0.213 |
| 6 | 5.0 | — | 25.1 | 99.2 | 0.048 | 0.151 | 0.145 | 0.230 | 0.101 | 0.232 | 0.223 | 0.337 |
| 7 | 5.0 | — | 48.7 | 199.9 | 0.039 | 0.088 | 0.111 | 0.146 | 0.085 | 0.155 | 0.185 | 0.237 |

| | to 1000 ml of H$_2$O for injection | | | | electrical | dimer [% rel. to paracetamol] | | |
|---|---|---|---|---|---|---|---|---|
| Ex. | paracetamol [g] | mannitol [g] | NaCl [g] | pH | conductivity [µS cm$^{-1}$] | start | 3 months 40° C. | 6 months 40° C. |
| 8 | 10.0 | 36.70 | — | 5.5 (native) | 11.15 | 0.0000 | 0.0126 | 0.0191 |
| 9 | 10.0 | — | 9.0 | 6.2 (NaOH) | 10430.00 | 0.0110 | 0.1881 | 0.3317 |
| 10 | 10.0 | 36.70 | — | 7.0 (NaOH) | 38.20 | 0.0053 | 0.0185 | 0.0218 |
| 11 | — | — | isotonic | native | 7660 | — | — | — |

Preferably, the composition is free of organic solvents, has a pH in the range from 5.5 to 7 and an oxygen content of at most 2.00 mg/l, more preferably at most 1.50 mg/l, even more preferably at most 1.25 mg/l, most preferably at most 1.00 mg/l and in particular at most 0.50 mg/l.

The parenteral administration of the composition according to the invention can basically be carried out in all customary ways, in particular intravenously, intra-arterially, subcutaneously, intramuscularly, intraventricularly, intracapsularly, intraocularly, intraspinally, intracisternally, intraperitoneally, intranasally or as an aerosol. Preferably, administration is carried out intravenously, wherein the composition is preferably present as an infusion solution.

The invention claimed is:

1. An aqueous pharmaceutical composition in the form of an infusion solution consisting essentially of water, paracetamol, a non-ionic isotonicizing agent, and cysteine, wherein the composition has an electrical conductivity of at most 200 µS cm$^{-1}$ wherein the composition does not contain any buffering agent, any C1-C6-alkanols, and any polyethylene glycol.

2. The composition according to claim 1, wherein the composition has a buffer capacity β of at most 5.0 mmol l$^{-1}$ pH$^{-1}$.

3. The composition according to claim 1, wherein it has a pH in the range from 5.0 to 7.0.

4. The composition according to claim 1, wherein the non-ionic isotonicizing agent is a sugar alcohol.

5. The composition according to claim 1, wherein the proportion by weight of the nonionic isotonicizing agent is greater than the proportion by weight of paracetamol.

6. The composition according to claim 1, wherein the composition has an osmolarity of at least 0.25 osmol/l$^{-1}$.

7. The composition according to claim 1, wherein the composition contains virtually no salt.

8. The composition according to claim 1, wherein the paracetamol is present in a concentration of 10.0±5.0 g l$^{-1}$.

9. The composition according to claim 1, wherein the content of paracetamol after storage at 60° C. for 4 weeks is at least 99.0% of the paracetamol originally contained in the composition.

10. The composition according to claim 1, wherein the composition is present in ready-to-use form.

11. The composition according to claim 1, wherein the composition has an osmolarity of at most 0.36 osmol/l$^{-1}$.

12. The composition according to claim 1, wherein the infusion solution is formulated for intravenous infusion over a period of time of 2 minutes to 24 hours.

13. The composition of claim 1, wherein the composition has an electrical conductivity of at most 100 µScm$^{-1}$.

14. The composition of claim 1, wherein the composition has an electrical conductivity of at most 70 µScm$^{-1}$.

15. The composition of claim 1, wherein the composition has an electrical conductivity of at most 50 µScm$^{-1}$.

16. The composition of claim 1, wherein the isotonicizing agent is mannitol.

17. The composition of claim 1, wherein the composition contains 10 g/liter paracetamol and no more than 36.7 g/liter mannitol.

18. The composition according to claim 1, wherein it contains no salt.

19. An aqueous pharmaceutical composition in the form of an infusion solution consisting of water, paracetamol, a nonionic isotonicizing agent, and cysteine, wherein the composition has an electrical conductivity of at most 200 µS cm$^{-1}$.

20. The composition of claim 18, wherein the composition has an electrical conductivity of at most 100 µScm$^{-1}$.

21. The composition of claim 18, wherein the composition has an electrical conductivity of at most 70 µScm$^{-1}$.

22. The composition of claim 18, wherein the composition has an electrical conductivity of at most 50 µScm$^{-1}$.

23. The composition of claim 18, wherein the isotonicizing agent is mannitol.

24. The composition of claim 23, wherein the composition contains 10 g/liter paracetamol and no more than 36.7 g/liter mannitol.

\* \* \* \* \*